United States Patent
Gadi

(10) Patent No.: US 10,134,147 B2
(45) Date of Patent: Nov. 20, 2018

(54) IDENTIFICATION OR DETERMINATION OF A LOAD BASED ON TEXTURE

(71) Applicant: Smiths Heimann SAS, Vitry-sur-Seine (FR)

(72) Inventor: Najib Gadi, Vitry-sur-Seine (FR)

(73) Assignee: SMITHS HEIMANN SAS, Vitry-sur-Seine (FR)

( * ) Notice: Subject to any disclaimer, the term of this patent is extended or adjusted under 35 U.S.C. 154(b) by 72 days.

(21) Appl. No.: 15/304,377

(22) PCT Filed: Mar. 27, 2015

(86) PCT No.: PCT/GB2015/050934
§ 371 (c)(1),
(2) Date: Oct. 14, 2016

(87) PCT Pub. No.: WO2015/159045
PCT Pub. Date: Oct. 22, 2015

(65) Prior Publication Data
US 2017/0046852 A1    Feb. 16, 2017

(30) Foreign Application Priority Data

Apr. 16, 2014  (GB) .................................. 1406887.8

(51) Int. Cl.
*G06T 7/40*   (2017.01)
*G06K 9/00*   (2006.01)
*G01N 23/04*  (2018.01)

(52) U.S. Cl.
CPC .............. *G06T 7/40* (2013.01); *G01N 23/04* (2013.01); *G06K 9/00* (2013.01); *G06K 2209/09* (2013.01); *G06T 2207/10004* (2013.01)

(58) Field of Classification Search
CPC ...... G01N 23/04; G06K 2209/09; G06K 9/00; G06T 2207/10004; G06T 7/40
See application file for complete search history.

(56) References Cited

U.S. PATENT DOCUMENTS

| 5,091,924 A | 2/1992 | Bermbach et al. |
| 5,600,303 A | 2/1997 | Husseiny et al. |
| 5,838,759 A * | 11/1998 | Armistead ............ B66C 19/007 378/57 |

FOREIGN PATENT DOCUMENTS

| EP | 0942295 A3 | 11/2001 |
| WO | 2006119603 A1 | 11/2006 |

OTHER PUBLICATIONS

UK Search Report dated Oct. 10, 2014 for Application No. GB1406887.8.

(Continued)

*Primary Examiner* — Siamak Harandi
(74) *Attorney, Agent, or Firm* — Kevin E. West; Advent, LLP

(57) ABSTRACT

In one embodiment, the disclosure relates to a method for inspecting a load (101) in a container (100), comprising: classifying (S2) one or more patches (11) of a digitized inspection image (10), the digitized inspection image (10) being generated by an inspection system (1) configured to inspect the container (100) by transmission of inspection radiation (3) from an inspection radiation source (31) to an inspection radiation detector (32) through the container (100), wherein the classifying (S2) comprises: extracting (S21) one or more texture descriptors (V, P) of a patch (11), and classifying (S22) the patch (11), by comparing the one or more extracted texture descriptors (V, P) of the patch (11) to respective one or more reference texture descriptors (Vr, Wr, Pr) corresponding to respective one or more classes (202) of reference items (201), the one or more reference (Continued)

texture descriptors (Vr, Wr, Pr) of each class of reference items (201) being extracted from one or more reference images (20) of the one or more reference items (201).

29 Claims, 14 Drawing Sheets

(56) References Cited

OTHER PUBLICATIONS

International Search Report dated Sep. 28, 2015 for International Appln. No. PCT/GB2015/050934.
Bastan, Muhammet et al., "Visual Words on Baggage X-Ray Images", Lecture Notes in Computer Science: Proceedings of the CAIP 2011, Aug. 29, 2011, Computer Analysis of Images and Patterns, Springer Berlin Heidelberg, Berlin, Heidelberg, pp. 360-368.
Duane, X. et al., "X-ray cargo container inspection system with few-view projection imaging", Nuclear Instruments & Methods in Physics Research, Section A: Accelerators, Spectrometers, Detectors, and Associated Equipment, Elsevier BV, North-Holland, NL, vol. 598, No. 2, Jan. 11, 2009, pp. 439-444.
Fitton, Greg et al., "A comparison of 3D interest point descriptors with application to airport baggage object detection in complex CT imagery", Pattern Recognition, Elsevier, GB, vol. 46, No. 9, Feb. 16, 2013, pp. 2420-2436.
Mery, D., "Computer vision technology for X-ray testing", Insight—Non-Destructive Testing and Condition Monitoring, vol. 56, No. 3, Mar. 1, 2014, pp. 147-155.
Mery, Domingo et al., "Automated Object Recognition in Baggage Screening using Multiple X-ray Views", Jan. 1, 2013, XP055200032.
Niercessian, S. et al., "Automatic Detection of Potential Threat Objects in X-ray Luggage Scan Images", Technologies for Homeland Security, 2008 IEEE Conference on, IEEE, Piscataway, NJ, USA, May 12, 2008, pp. 504-509.
Oertel, C. et al., "Identification of Objects-of-Interest in X-Ray Images", Applied Imagery and Pattern Recognition Workshop 2006, AIPR 2006, 35th IEEE, IEEE, PI, Oct. 11, 2006, p. 17.
Schmidt-Hackenberg, Ludwig et al., "Visual cortex inspired features for object detection in X-ray images", Pattern Recognition (ICPR), 2012 21st International Conference on, IEEE, Nov. 11, 2012, pp. 2573-2576.

* cited by examiner

Cigarettes Data
Base (class 1)

Vr1(m1, σ1, m2, σ2,...)
Vr2(m1, σ1, m2, σ2,...)
Vr3(m1, σ1, m2, σ2,...)
Vr4(m1, σ1, m2, σ2,...)
Vr5(m1, σ1, m2, σ2,...)
Vr6(m1, σ1, m2, σ2,...) ← 202
Vr7(m1, σ1, m2, σ2,...)
Vr8(m1, σ1, m2, σ2,...)
Vr9(m1, σ1, m2, σ2,...)
Vr10(m1, σ1, m2, σ2,...)
Vr11(m1, σ1, m2, σ2,...)
Vr12(m1, σ1, m2, σ2,...)
Vr13(m1, σ1, m2, σ2,...)
Vr14(m1, σ1, m2, σ2,...)
Vr15(m1, σ1, m2, σ2,...)
Vr16(m1, σ1, m2, σ2,...)
...
...
...
⎱ 200

«others» Data Base
(class 2)

Wr1(m1, σ1, m2, σ2,...)
Wr2(m1, σ1, m2, σ2,...)
Wr3(m1, σ1, m2, σ2,...)
Wr4(m1, σ1, m2, σ2,...)
Wr5(m1, σ1, m2, σ2,...)
Wr6(m1, σ1, m2, σ2,...) ← 202
Wr7(m1, σ1, m2, σ2,...)
Wr8(m1, σ1, m2, σ2,...)
Wr9(m1, σ1, m2, σ2,...)
Wr10(m1, σ1, m2, σ2,...)
Wr11(m1, σ1, m2, σ2,...)
Wr12(m1, σ1, m2, σ2,...)
Wr13(m1, σ1, m2, σ2,...)
Wr14(m1, σ1, m2, σ2,...)
Wr15(m1, σ1, m2, σ2,...)
Wr16(m1, σ1, m2, σ2,...)
...
...
...
⎱ 200

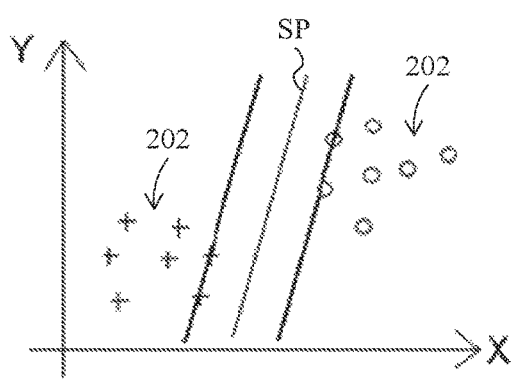
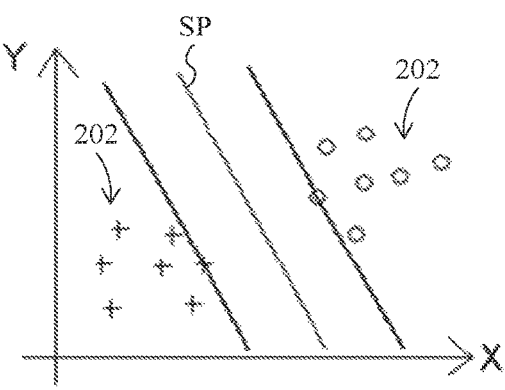
Fig. 13A          Fig. 13B
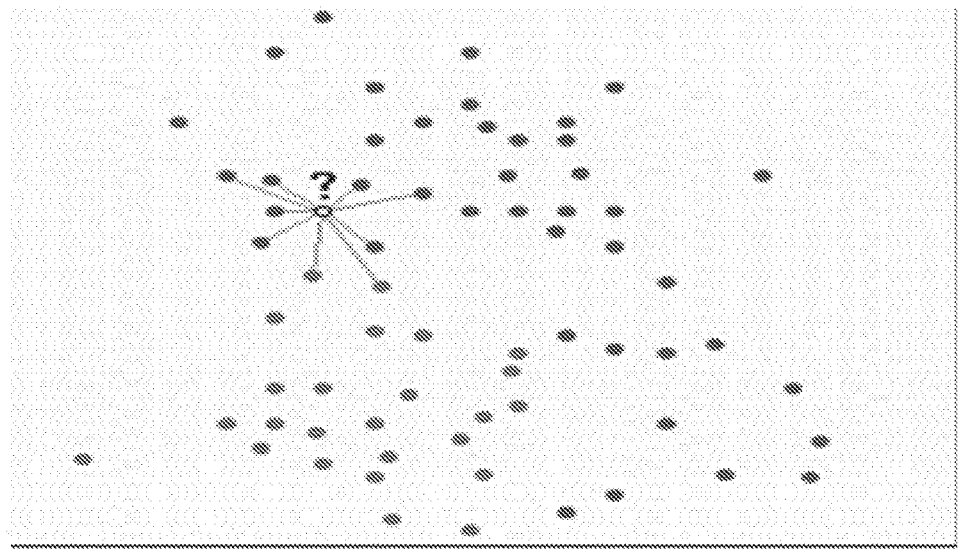
Fig. 14

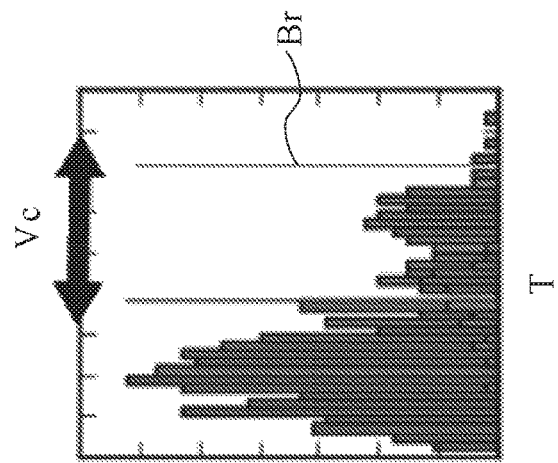
Fig. 15C
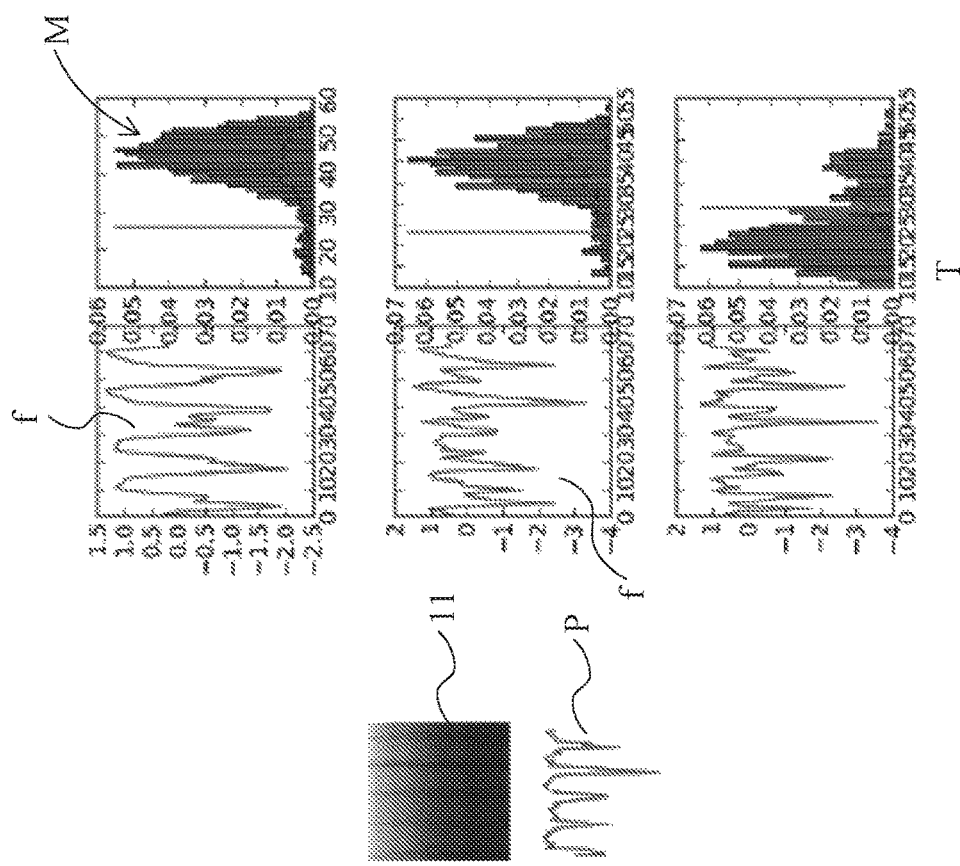
Fig. 15A
Fig. 15B

IDENTIFICATION OR DETERMINATION OF A LOAD BASED ON TEXTURE

FIELD OF THE INVENTION

The present disclosure relates to methods and systems of inspection by transmission of radiation, and more particularly to inspection for identification and/or determination of a load in a container.

BACKGROUND OF THE INVENTION

Known methods and systems of inspection use transmission of radiation through a container to determine the nature of its load. It is sometimes difficult to determine the nature of the load, as some different items and/or different compositions appear to be similar on inspection images generated by the known methods and systems of inspection.

PRESENTATION OF THE FIGURES

Embodiments of the disclosure will now be described, by way of example only, with reference to the accompanying drawings, in which.

Figure 9:
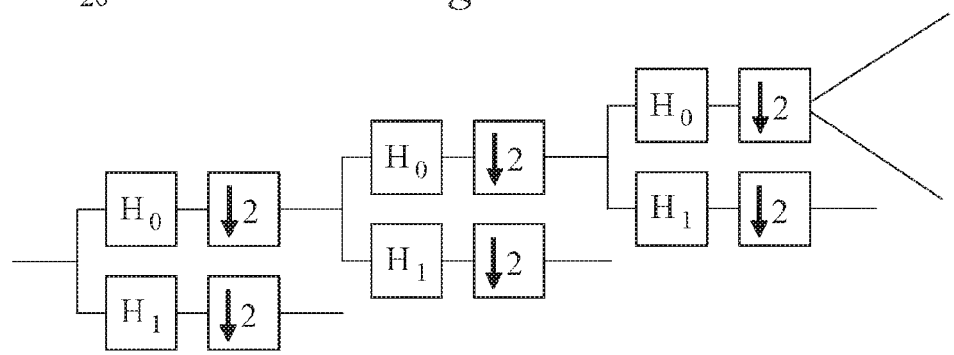
Figure 10A:
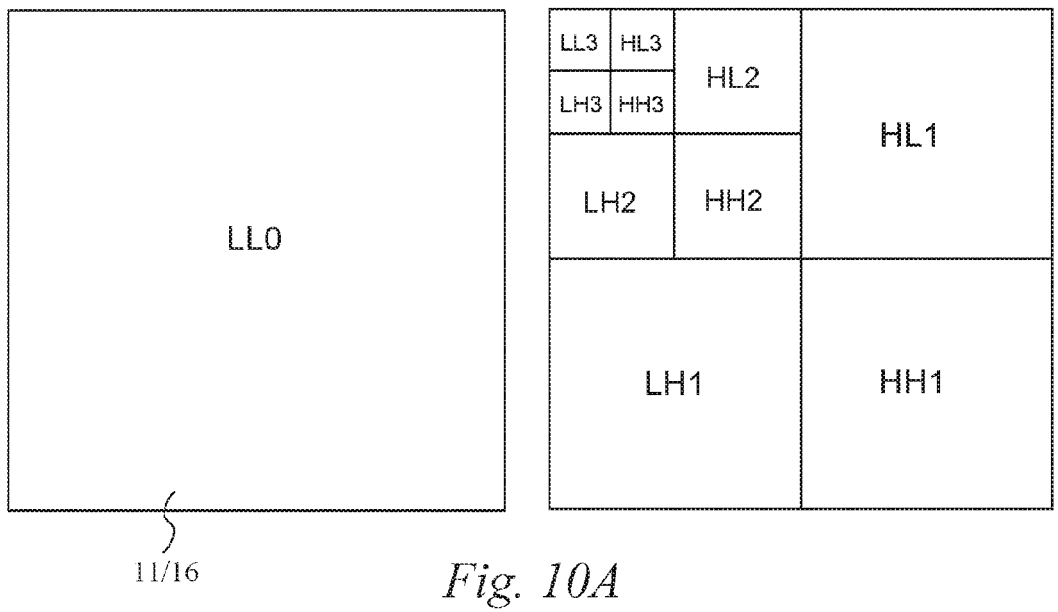
Figure 10B:
Figures 11A, 11B, 11C:
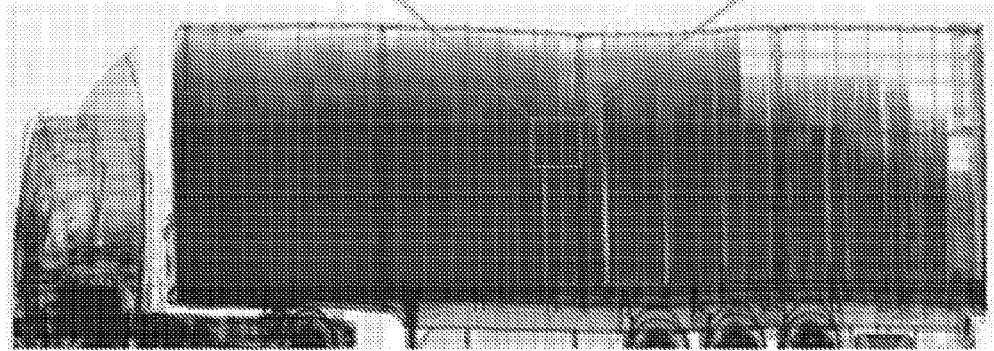
Figure 12A:
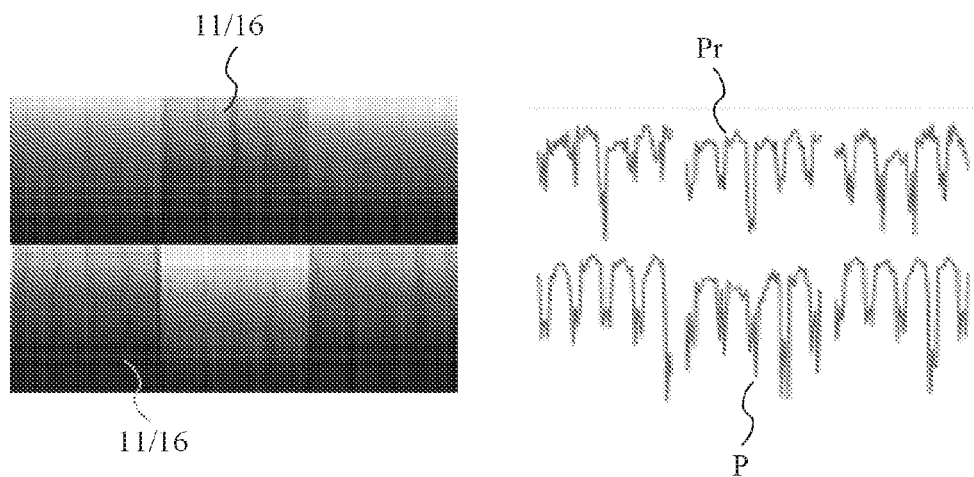
Figure 12B:
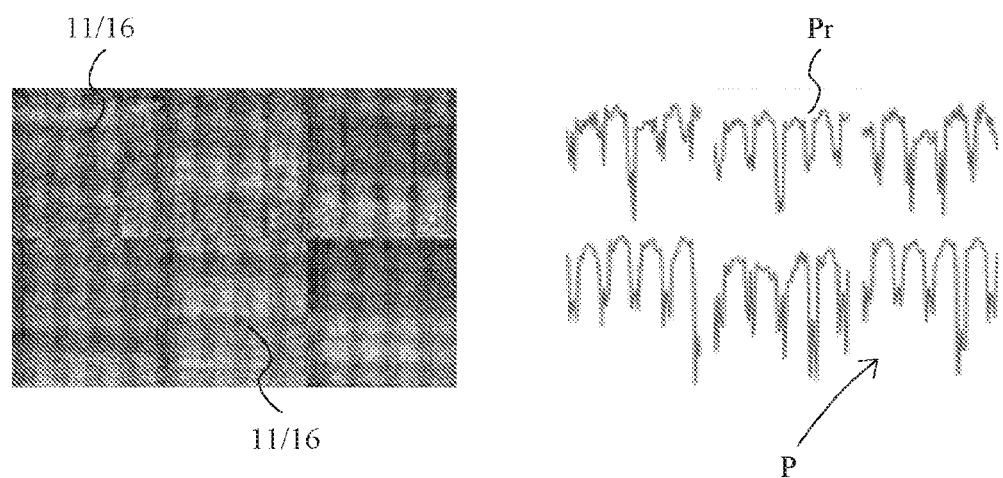
Figure 16A:
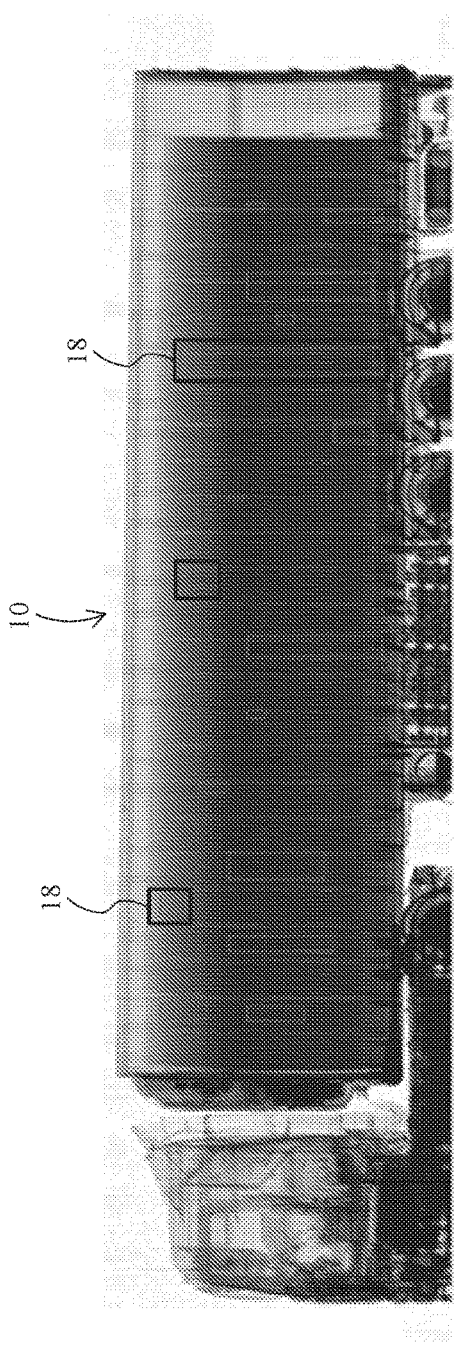
Figure 16B:
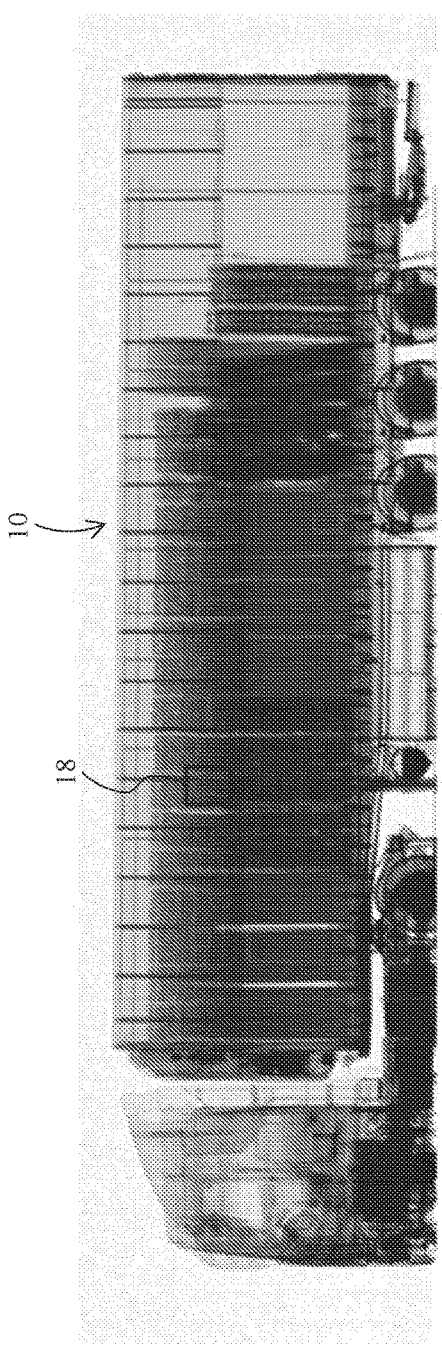
Figure 17A:
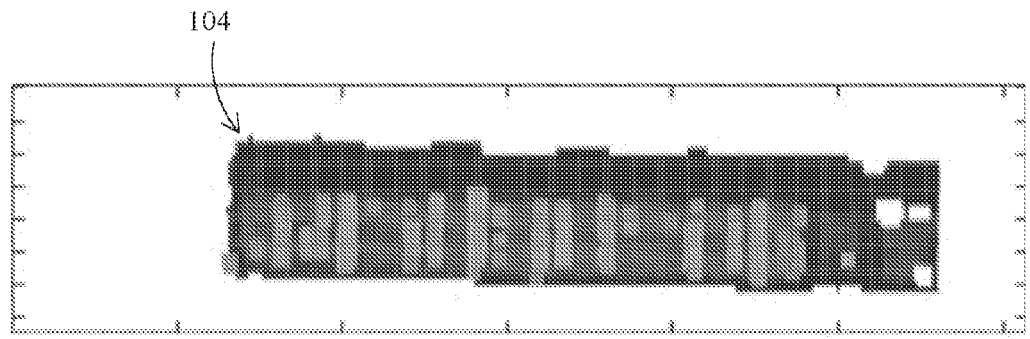
Figure 17B:
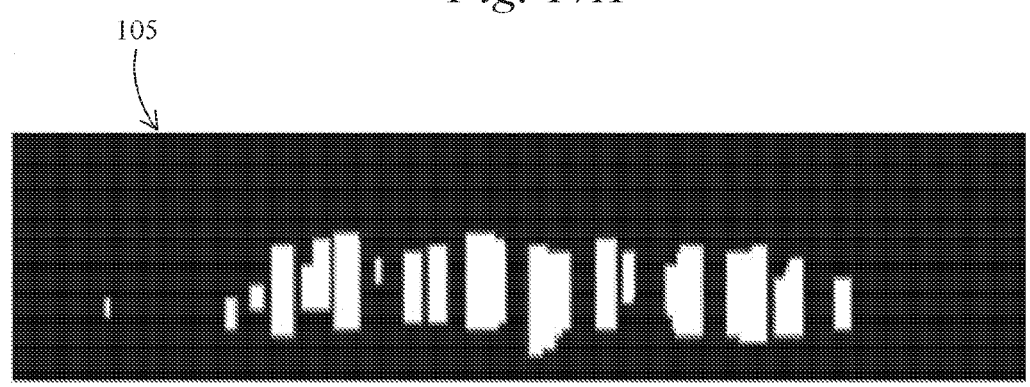

FIG. 9 schematically illustrates an example of a texture features extractor using Quadrature Mirror Filters, QMF;

FIG. 10A schematically illustrates an example of a decomposition of an image into three decomposition scales using a texture features extractor using Quadrature Mirror Filters, QMF;

FIG. 10B illustrates an example of a decomposition of an image into two decomposition scales using a texture features extractor using Quadrature Mirror Filters, QMF;

FIG. 11A schematically illustrates an example of a reference class comprising a plurality of texture descriptors Vr, referred to as "cigarettes" database or class 1;

FIG. 11B schematically illustrates an example of a reference class comprising a plurality of texture descriptors Wr, referred to as "non-cigarettes" database or class 2;

FIG. 11C schematically illustrates an example of a texture descriptor V comprising a plurality of texture features, the texture descriptor V describing a patch to be classified;

FIG. 12A schematically illustrates examples of an impact of diffusion on a plurality of patches (left-hand side), and examples of respective dedicated texture descriptors of the plurality of patches (right-hand side);

FIG. 12B schematically illustrates examples of an impact of noise on a plurality of patches (left-hand side), and examples of respective dedicated texture descriptor of the plurality of patches (right-hand side);

FIG. 13A schematically illustrates an example of a classifier using a Support Vector Machine (SVM) technique;

FIG. 13B schematically illustrates another example of a classifier using a Support Vector Machine (SVM) technique;

FIG. 14 schematically illustrates an example of a classifier using a k nearest neighbours (k-NN) technique;

FIG. 15A schematically illustrates an example of a patch to be classified with an example of its respective dedicated texture descriptor;

FIG. 15B schematically illustrates an example of a bench of filters and the corresponding thresholds of decision;

FIG. 15C schematically illustrates a response of the patch of FIG. 15A to the bench of FIG. 15B, with its corresponding value of confidence;

FIGS. 16A and 16B schematically illustrate examples of equalized images showing false positives; and FIG. 17A schematically illustrates an image showing a probability in each patch of the inspection image;

FIG. 17B schematically illustrates an example generated binary image; and

Figure 18:
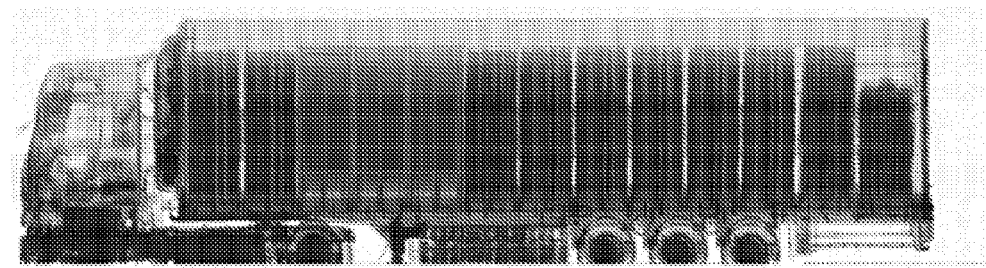

FIG. 18 schematically illustrates a final image as displayed to a user.

In the Figures like reference numerals are used to indicate like elements.

DESCRIPTION OF EXAMPLE EMBODIMENTS

Overview

Embodiments of the disclosure relate to a method for inspecting a load in a container by extracting one or more texture descriptors from patches of a digitized inspection image of the load, and by classifying the corresponding patches into reference classes of items using the extracted one or more texture descriptors. The classifying may involve comparing the extracted one or more texture descriptors with one or more reference texture descriptors corresponding to the reference classes. The classifying may enable e.g., detection and/or identification of the load, or may enable identification of a composition of at least a part of the load. The extraction of the texture descriptors may enable the detection and/or identification where mere analysis, without using the texture of at least a zone of interest of the image, does not allow discrimination between different items or compositions on the inspection image. The detection and/or identification may particularly be advantageous in cases where the load and/or the composition to be detected and/or identified include high value and/or contraband items and/or compositions, such as cigarettes, bank notes, drugs (such as cannabis or cocaine), medications, pills, beans (such as coffee), etc.

Embodiments of the disclosure use texture descriptors, texture extractors and/or texture classifiers which may allow detection and/or identification of the load and/or its composition, even with a relatively small number of reference texture descriptors in the reference classes (for example a number of an order of magnitude of 1000). Alternatively or additionally, embodiments of the disclosure may enable detection and/or identification of the load and/or its composition, even with a relatively high amount of noise and/or diffusion in, and/or a relatively low resolution of, the inspection images. Alternatively or additionally, embodiments of the disclosure may enable identification and/or detection in a relative short period of time, i.e. in an order of magnitude of a second.

Embodiments of the disclosure use classifying one or more zones of the inspection image, and thus may enable identification and/or detection, even when at least a part of the load is superimposed with a screen blocking the transmission of the inspection radiation.

Detailed Description of Example Embodiments

Figure 7:
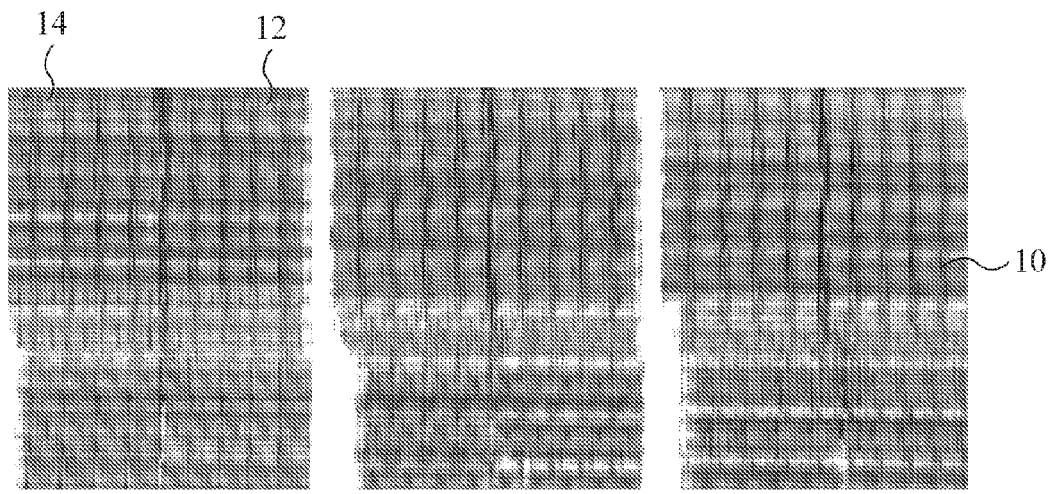
FIG. 7 illustrates examples of zones of inspection images in accordance with the present disclosure, comprising examples of cigarettes patches.

As illustrated in FIG. 7, a texture in an image 10 is a quasi-periodic or random repetition of basic elements 14 having identical macroscopic visual properties. The basic elements 14 are sometimes called 'texels' (a short version for 'texture elements'). The texture in an image 10 of an item is one of the parameters which may be used to identify the item and/or its composition. As a non-limiting example, a texture may be identified in an image of cigarettes, since:
- the cigarettes are located in packs containing a specific, regular, number of cigarettes (usually 20 cigarettes a pack),
- the packs are located in cartons containing a specific, regular, number of packs (usually 10 packs a carton),
- the cartons are located in boxes containing a specific, regular, number of cartons (for example 10 cartons a box), and
- the boxes are located in pallets containing a specific, regular, number of boxes to obtain a specific volume (for example approximately 1 m$^3$ in Europe and approximately 1.25 m$^3$ in the US).

The texture of the image 10 may be described by at least one texture descriptor comprising texture features. As described in further detail below, the texture descriptor may be extracted from values of pixels 12 of the image 10 and/or from spatial mutual relationships between the pixels 12 of the image 10 corresponding to the structure of the image 10.

Figure 1:
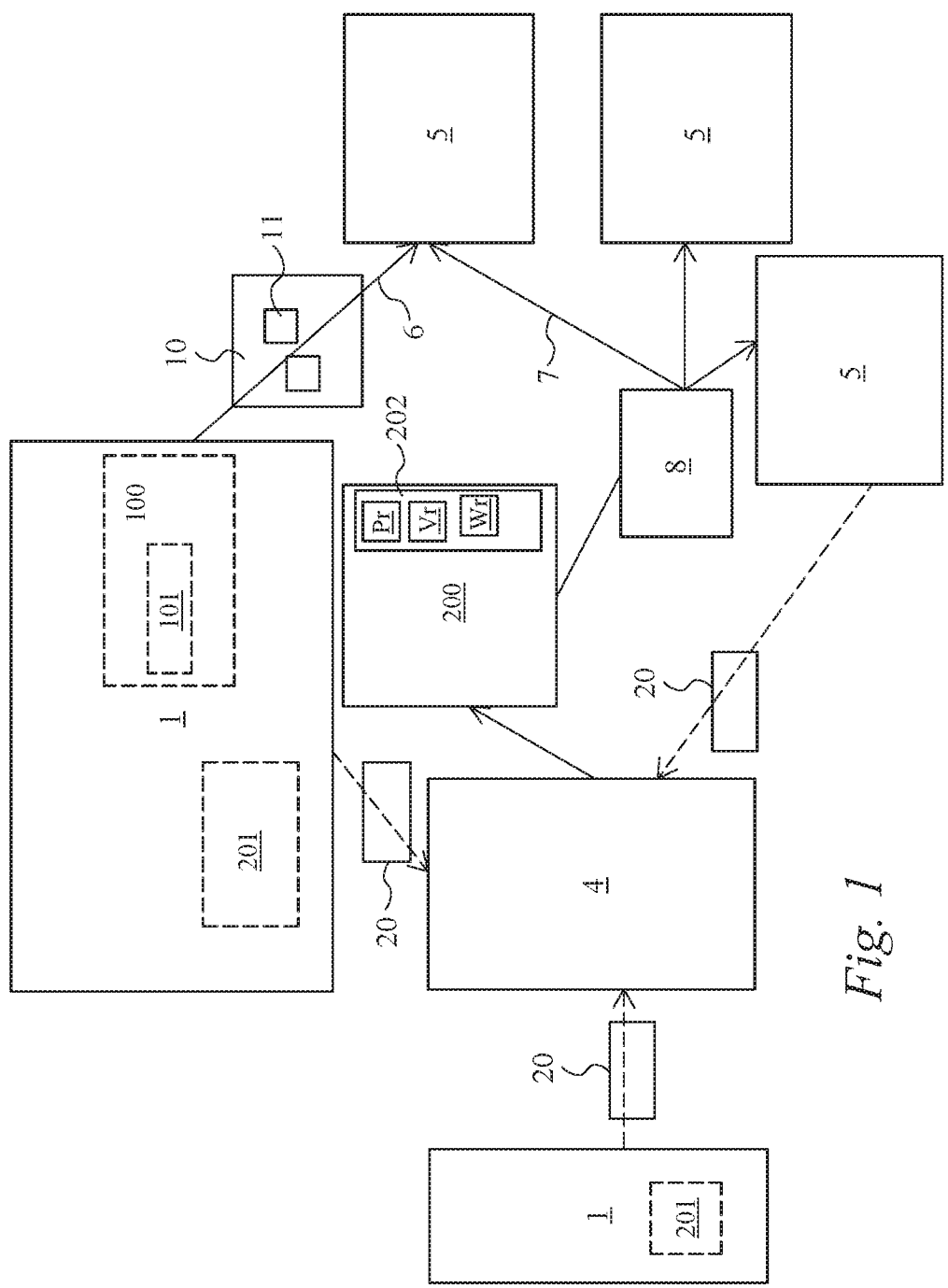
FIG. 1 is diagrammatic view that illustrates an example analyser in accordance with the present disclosure, configured to be connected to an inspection system in accordance with the present disclosure.

FIG. 1 illustrates an analyser 5 configured to classify one or more patches 11 of one or more digitized inspection images 10 of a load 101 in a container 100.

Each of the images 10 may be generated by an inspection system 1.

As will be apparent in more detail below, the analyser 5 may be configured to receive the one or more images 10 from the system 1, for example over a communication network 6 which may be wired and/or may be wireless. The analyser 5 conventionally comprises at least a processor and a memory in order to carry out an example method according to the disclosure.

As explained in further detail below in relation to FIGS. 2 and 3, the inspection system 1 is configured to inspect the container 100 by transmission of inspection radiation 3 from an inspection radiation source 31 to an inspection radiation detector 32 through the container 100.

Figure 2:
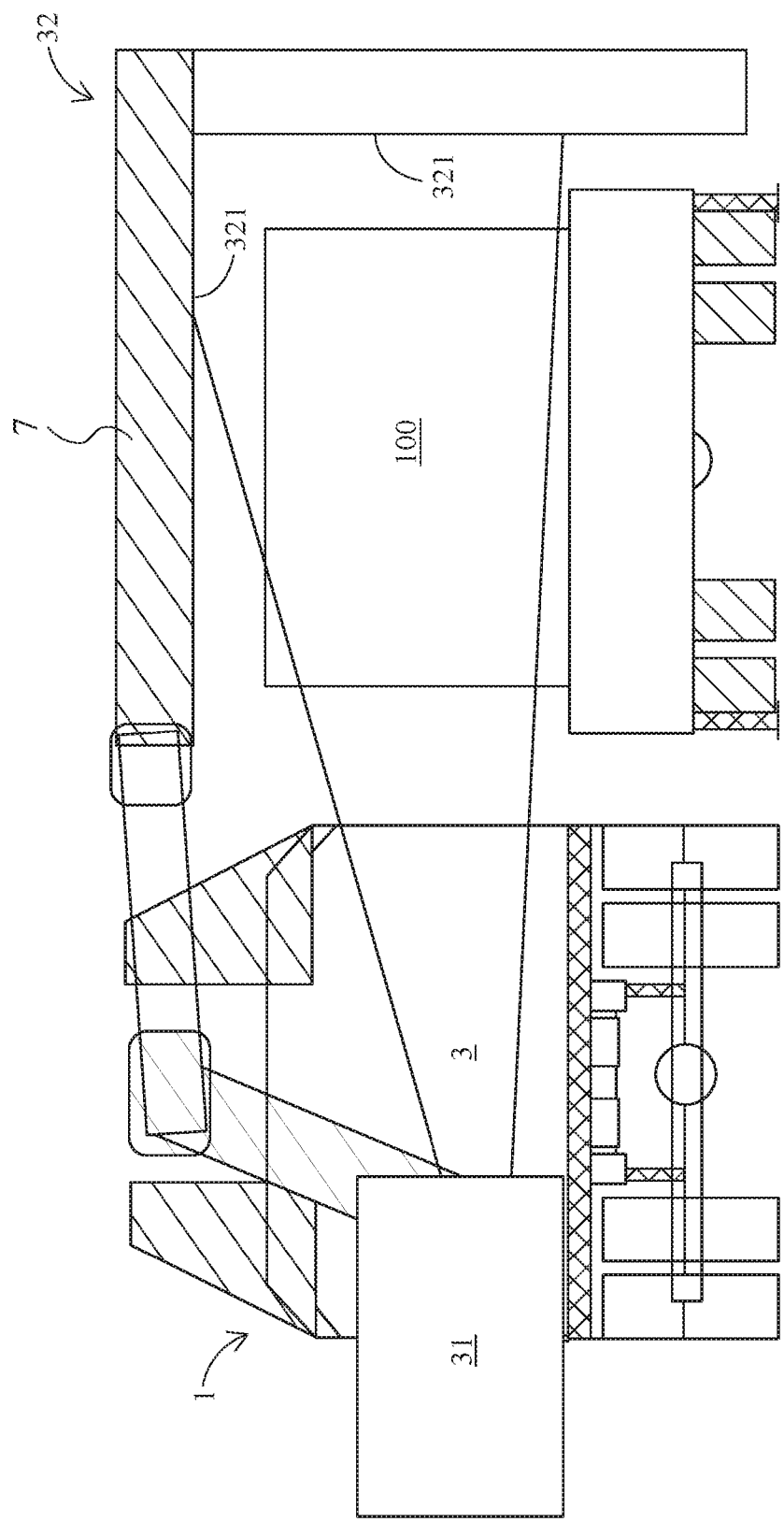
FIG. 2 is a rear view that illustrates an example of a mobile inspection system in accordance with the present disclosure, in an inspection mode.
Figure 3:
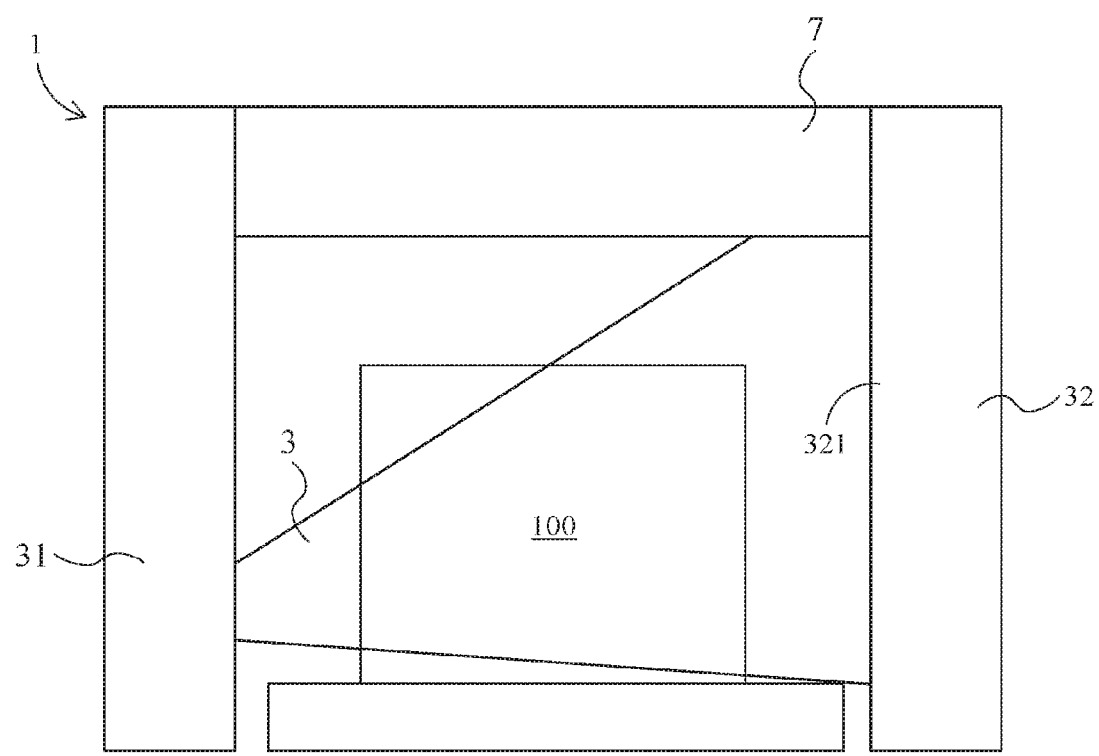
FIG. 3 is a rear view that illustrates an example of a static inspection system in accordance with the present disclosure, in an inspection mode.

FIGS. 2 and 3 illustrate that the container 100 may be a trailer and/or a boot of a vehicle such as a truck, a van and/or a car, and/or may be a shipping container. It is appreciated that the container 100 may be any type of container, and thus may be a suitcase in some examples. The radiation source 31 is configured to cause inspection of the load 101 through the material (usually steel) of walls of the container 100, e.g. for detection and/or identification of high value and/or contraband items and/or compositions, such as cigarettes, bank notes, drugs, medications, pills, beans (such as coffee beans), etc.

The system 1 is configured to, in the inspection mode, cause inspection of the container 100, in totality (i.e. the whole container 100 is inspected) or partially (i.e. only a chosen part of the container is inspected, e.g., typically, when inspecting a vehicle, a cabin of the vehicle may not be inspected, whereas a rear part of the vehicle is inspected).

In the example illustrated by FIG. 2, the inspection system 1 may be mobile and may be transported from a location to another location (the system 1 may comprise an automotive vehicle), and in the example illustrated by FIG. 3, the inspection system 1 may be static with respect to the ground and cannot be displaced.

A type of the inspection system 1 may be characterized by an energy and/or a dose of the inspection radiation 3.

In the examples illustrated by the Figures, the inspection radiation source 31 comprises an X-ray generator. The energy of the X-rays may be comprised between 1 MeV and 15 MeV, and the dose may be comprised between 2 mGy and 20 Gy (Gray). In the example illustrated by FIG. 2, the power of the X-ray source 31 may be e.g., between 500 keV and 9.0 MeV, typically e.g., 2 MeV, 3.5 MeV, 4 MeV, or 6 MeV, for a steel penetration capacity e.g., between 150 mm to 350 mm, typically e.g., 200 mm (7.9 in). In the example illustrated by FIG. 2, the dose may be e.g., between 20 mGy and 50 mGy. In the example illustrated by FIG. 3, the power of the X-ray source 31 may be e.g., between 4 MeV and 10 MeV, typically e.g., 9 MeV, for a steel penetration capacity e.g., between 300 mm to 450 mm, typically e.g., 410 mm (16.1 in). In the example illustrated by FIG. 3, the dose may be 17 Gy.

In the examples illustrated by the Figures, the inspection radiation detector 32 comprises, amongst other conventional electrical elements, radiation detection lines 321, such as X-ray detection lines. The inspection radiation detector 32 may further comprise other types of detectors, such as optional gamma and/or neutrons detectors, e.g., adapted to detect the presence of radioactive gamma and/or neutrons emitting materials within the container 100, e.g., simultaneously to the X-ray inspection. In the example illustrated in FIG. 2, the inspection radiation detector 32 may also comprise an electro-hydraulic boom 7 which can operate in a retracted position in a transport mode (not illustrated in the Figures) and in an inspection position (FIG. 2). The boom 7 may be operated by hydraulic activators (such as hydraulic cylinders). In the example illustrated in FIG. 3, the inspection radiation detector 32 may also comprise a structure and/or gantry 7. The detection lines 321 may be mounted on the boom 7 (FIG. 2) or structure and/or gantry 7 (FIG. 3), facing the source 31 on the other side of the container 100.

In order to inspect the container 100, in the example illustrated by FIG. 2, the system 1 may comprise a motion generation device so that the system 1 may be displaced, the container 100 being static (this mode is sometimes referred to as a 'scanning' mode). Alternatively or additionally, the motion generation device may cause the container 100 to be displaced, the system 1 being static with respect to the ground (FIG. 3). Alternatively or additionally, in a 'pass-through' mode the system 1 does not comprise a motion generation device and the container moves with respect to the system 1, the system 1 being static with respect to the ground.

In some examples, the radiation 3 may be transmitted through the container 100 (the material of the container 100 being thus transparent to the radiation), while the radiation may, at least partly, be reflected by the load 101 located in the container 100 (the material and/or composition of the load located in the container 100 being thus only partly transparent to the radiation 3, and partly reflective to the radiation 3—in that case, detectors may be placed to receive the radiation reflected by the load 101).

Figure 4:
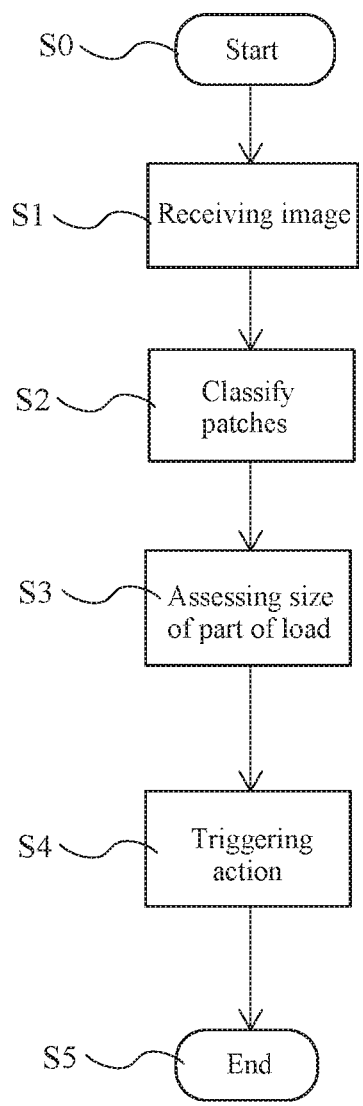
FIG. 4 is a flowchart that illustrates an example method in accordance with the present disclosure.
Figure 5:
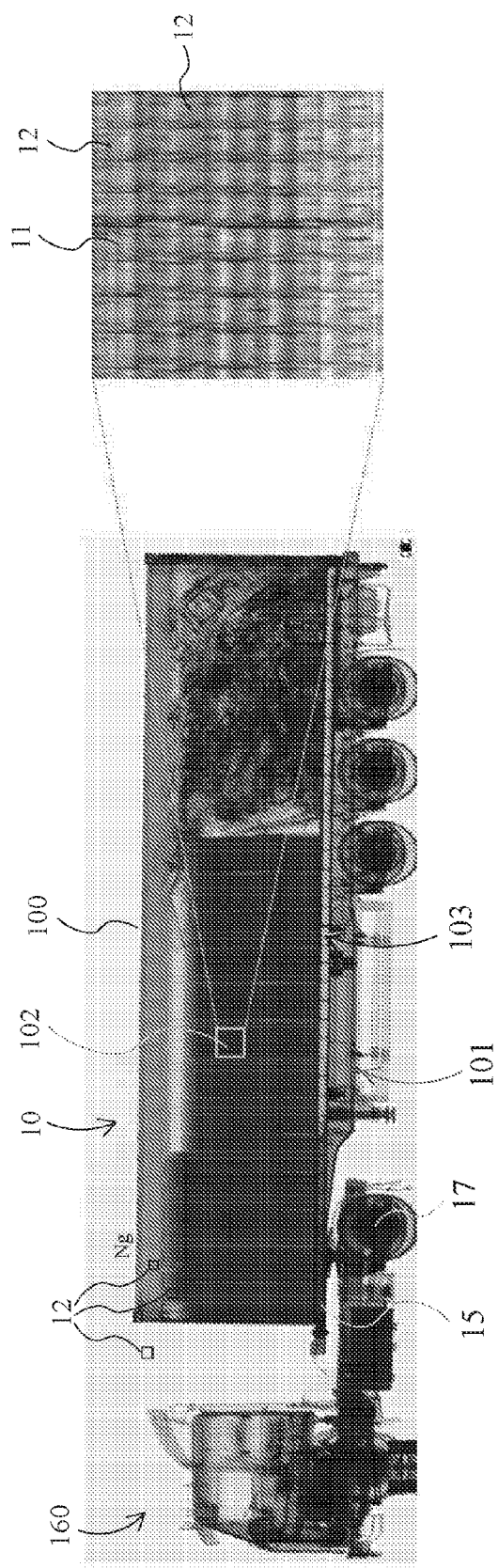
FIG. 5 illustrates an example inspection image in accordance with the present disclosure, comprising examples of cigarettes patches.

The example method illustrated by FIG. 4 may comprise receiving, at S1, one or more digitized images 10 from the inspection system 1. As illustrated in FIG. 5, each digitized image 10 comprises a plurality of pixels 12. At least a value Ng representative of the transmission of the inspection radiation 3 through the container 100 is associated with each pixel 12. Each pixel 12 is associated with a portion of the space and may be associated with a 102 of the load 101.

At S2, the analyser 5 classifies one or more patches 11 of the digitized inspection image 10. Each of the patches 11 is a division of the image 10, for example the image 10 may be divided into successive patches 11. In some examples, the analyser 5 may divide the received image 10 into the patches 11. Alternatively or additionally, the analyser 5 may receive the image 10 from the inspection system 1 already divided into the patches 11. The patches may be part of a selection 15 of patches 11, such as to reduce processing time by only classifying patches of interest, as explained in further detail below.

In some examples, successive patches 11 may be overlapping each other. The overlap between two successive patches 11 may take any extent, such as for example the overlap may be comprised between 10% and 90%. It is appreciated that an overlap of 10% generally reduces the number of patches 11 to be processed in an image 10, and thus reduces the time of processing, at a cost of a possible less accurate result, whereas an overlap of 90% generally increases the number of patches 11 to be processed in an image 10, and thus increases the time of processing, but gives a more accurate result. As an advantageous compromise, the overlap may be equal to 50%.

Each of the patches 11 may be of any dimension or form. However, as will be apparent in the specification below, each patch 11 may form a square, with a same number of pixels on each side of the patch 11. This may be advantageous in some examples of the disclosure, some of the algorithms requiring square patches. In an example, the number of pixels on each side of the patch 11 may be 64, and the dimension of each patch may be then 64×64 pixels.

In some examples, the method may further comprise selecting, for further processing, only patches 11 having a mean value Mg (Mg being the mean of the values of the pixels 12 of a patch) such that:

T1<Mg<T2, where: T1 is a minimum threshold value for items of interest inspected by the inspection system 1; and
T2 is a maximum threshold value for items of interest inspected by the inspection system 1.

Pixels 12 with values Ng above T2 usually correspond to pixels associated with background 160 in the image 10, and pixels 12 with values Ng below T1 are usually zones 17 too dark for any detection. The selection of the patches 11 decreases the number of patches 11 to process, and thus saves some processing time. For example, for values Ng encoded on 16 bits (from 0 to 65535), T1 may be for example equal to 2000 and T2 may be for example equal to 55000.

As explained in greater detail below, the method illustrated in FIG. 4 may comprise, at S3, an optional assessing of a size of a part 103 of the load 101 corresponding to a plurality of selected patches 11 classified in a same class, and only items with parts 103 having a size above a threshold size may be processed. This may reduce the number of false alarms. It is appreciated that the size may depend on the item. For example, it might be that parts 103 of cigarettes below a threshold corresponding to half the size of a pallet (i.e. approximately ½ m³ in Europe) may not be processed. The threshold size may be smaller in the case of drugs or bank notes for example.

At S4, the method comprises triggering an action based on the result of the classifying performed at S2.

As explained in greater detail below, the action may be:
determining a composition of the part 103 of the load 101 corresponding to the selected patch 11 of the inspection image 10,
displaying the digitized inspection image with one or more determined compositions for one or more parts 103 of the load 101,
issuing an alarm, and/or
sending one or more selected patches 11 to a controller 4.

In the example illustrated by FIG. 6, the classifying performed at S2 may comprise, for one or more patches 11, for example in a selection 15 of one or more patches 11 as explained in further detail below:
extracting, at S21, one or more texture descriptors V or P, for example based on the value of the pixels 12 located in the selected patch 11 as explained in further detail below, and
classifying, at S22, the selected patch 11, by comparing the one or more extracted texture descriptors of the selected patch 11 to one or more reference texture descriptors Vr, Wr or Pr corresponding to one or more classes 202 of reference items 201.

As already explained, the reference items 201 may be, as non-limiting examples, cigarettes, bank notes, drugs (such as cannabis or cocaine), medications (such as pills or tablets), pills, beans (such as coffee beans), etc. There may thus be a class 202 for cigarettes, a class 202 for bank notes, a class 202 for cannabis, etc.

As explained in greater detail below, the reference texture descriptors of each class 202 of reference item 201 may be extracted from one or more reference images 20 of the one or more reference items 201, for example inspected by the inspection system 1.

In the example illustrated by FIG. 1, the reference texture descriptors Vr, Wr or Pr, for example forming the classes 202, may be stored in a reference database 200. In some examples, the database 200 may comprise respective reference texture descriptors Vr, Wr or Pr (and thus for example the corresponding classes 202) for each type of inspection system 1.

Figure 8:
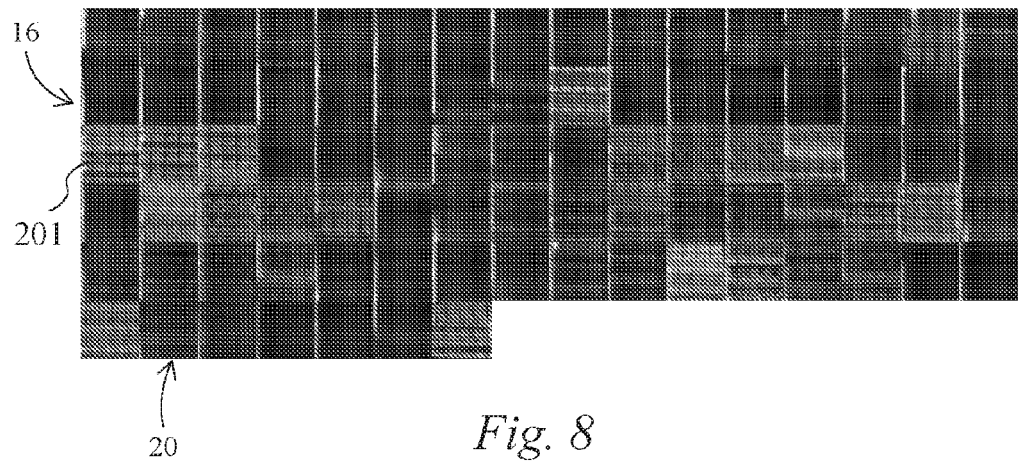
FIG. 8 illustrates examples of reference cigarettes patches in accordance with the present disclosure.

In the example illustrated by FIG. 8, the reference texture descriptors of the class cigarettes 202 may be extracted from patches 16 of reference images 20 of cigarettes, as inspected by the inspection system 1.

It will be appreciated that in examples of the method in accordance with the disclosure, the analyser 5 may be configured to retrieve the reference texture descriptors Vr, Wr or Pr from the database 200 over a communication network 7, thanks to a communication server 8 configured to provide a remote data management system. Alternatively or additionally, the database 200 may be at least partially located in the analyser 5.

In the example illustrated by FIG. 1, the server 8 may also provide access to the database 200 to a plurality of geographically distributed analysers 5, over the network 7.

As already stated, in some examples, the database 200 may be populated from reference items 201 inspected by the inspection system 1.

In the example illustrated by FIG. 1, the inspection system 1 may thus send reference images 20 to the controller 4 which may be further configured to extract the corresponding reference texture descriptors and thus populate the database 200, for example during a phase of setting up.

In the example illustrated by FIG. 1, one or more inspection systems 1 (of same or different types) may also send reference images 20 of reference items 201 to the controller 4 in order to further populate the database 200.

Alternatively or additionally, the analyser 5 may also send one or more selected patches 11 to the controller 4 once they have been classified in a class 202, in order to further populate the database 200 (the one or more selected patches 11 may be then considered as reference patches). This allows enriching and/or updating the database 200.

It will be appreciated that the disclosure may be applied to detection and/or identification of any type of item and/or composition. However, a non-limiting example for detection and/or identification of cigarettes will now be described.

First the reference classes 202 are built, and they may be referred to as class 1 for "cigarettes" and class 2 for "non-cigarettes".

In order to build the class 1, a set of reference images 20 containing only images of cigarettes may be divided into patches 16 having a size of 64×64 pixels. This size of patch is advantageous, at least because a pallet of cigarettes usually occupies about 70 pixels on the detection lines 321 of the inspection system 1. A texture descriptor (such as a vector having texture features as its dimensions, as described in more detail below) may then be extracted for each reference cigarettes patch 16. Examples of methods of extraction of the descriptors will be described in more detail below. The set of all these texture descriptors (such as vectors) is the reference class 1.

Similarly, a set of reference images 20 containing only images of non-cigarettes items may be divided into patches 16 with the size 64×64 pixels. A texture descriptor may then be extracted for each reference non-cigarettes patch 16. The set of all these descriptors is the reference class 2.

In some embodiments, the method may comprise a validation step of the reference classes and/or of the method by cross-validation. The cross-validation may comprise a step of classifying a subset of one or more patches 16 of the reference images 20 using the other patches 16 of the reference images 20.

Then, when one wants to determine if an inspection image 10 contains cigarettes or not, the image 10 is divided into patches 11 of the same size as the patches 16 constituting the two reference classes 202 (i.e. 64×64 pixels). Each patch 10 is considered as being an object to be classified.

The analyser 5 may extract the texture descriptor as for the reference descriptors. Then a classification method may be applied in order to classify the patches 11. Examples of methods of classification will be described in more detail below.

As already stated, the method may comprise classifying one or more overlapping successive patches 11. The overlap between two successive patches may be comprised between 10% and 90%, and may be preferably equal to 50%.

Once the patches 11 are classified, the image may be equalized, and an action may be triggered.

The action may comprise determining a composition of the part 103 of the load 101 corresponding to the selected patch 11 of the inspection image 10, such as cigarettes or drugs. The action may also be displaying the digitized inspection image with one or more determined compositions for one or more parts 103 of the load 101, as illustrated in FIG. 18. The display may use a code of colours for the different items and/or compositions for ease of inspection by a user. An alarm (visual and/or aural) may be issue as a response to the identification and/or detection of an item and/or composition.

Each of the texture descriptor may be a generic descriptor and/or a descriptor dedicated to a load 101 and/or a reference item 201.

As explained in greater detail below, the generic descriptor may be extracted using one or more extractors among the following: a response to a bench of filters; a Haralick method implementing a matrix of co-occurrence; and/or a quadrature mirror filter, QMF.

In some examples, the response to a bench of filters may implement, for example, Gabor filters, i.e. filters generated from a Gabor function on a plurality of scales and orientations. Gabor filters may allow extraction of textures, contours, lines and points with different orientations in patches 11 and/or 16.

In some examples, each patch 11 and/or 16 may be filtered by a plurality of bi-directional Gabor filters, which correspond to a convolution with a cosine kernel, weighted by a Gaussian window. The bi-directional Gabor filters may be equivalent to a local Fourier transform using a Gaussian window. The response to a bench of filters may thus enable to filter locally a bandwidth of frequencies.

For example, let pa represent the patch 11 and/or 16, and

Df its frequency domain.

Then a texture descriptor V may be calculated by convolution of pa by g, g being a Gabor filter such that:

$$V(f) = \int_{Df} pa(f+\varepsilon) \cdot g(\varepsilon) \cdot d\varepsilon$$

with g being a Gabor filter in 2D (i.e. on the frequencies (i,j)) such that:

$$g_{\lambda,\vartheta,\phi}(i,j) = \exp\left(-\frac{x^2 + \phi^2 y^2}{2\varpi^2}\right) \cos\left(2\pi \frac{x}{\lambda} + \phi\right)$$

with:

$x = i \cos \vartheta + j \sin \vartheta$ $\varpi = 0.56\lambda$ $y = -i \sin \vartheta + j \cos \vartheta$ $\phi = 0.5$.

and θ and λ being chosen filter parameters.

In some examples, two benches of filters g may be used, with the same parameters θ and λ as the parameters θ and λ set out in the article "Comparison of texture features based on Gabor filters", by Grigorescu et al., IEEE Transactions on Image Processing, 2002, vol. 11, #10, p. 1160-1167. In one of the two benches, the Gabor kernel may be symmetrical (Φ=0), and in the second of the two benches, the Gabor kernel may be anti-symmetrical (Φ=−π/2). Each bench contains 24 Gabor filters of frequency 1/λ (with 1/λ being successively equal to 23, 31 and 47) and of orientation θ=kπ/8 (with k being successively equal to 0, 1, 2, 3, 4, 5, 6 and 7).

Therefore in some examples, as a response to each of the two benches of 24 filters as described above, a descriptor under the form of a vector V with 24 dimensions may be extracted, for each pixel 12 in the patch 11 and/16 of the image 10 or 20. The obtained generic descriptor V may thus comprise 24 texture features.

The two vectors V obtained from the symmetric and anti-symmetric benches may also be combined into a single texture descriptor which may be called "Gabor energy" Ve (the Gabor energy may be related to a modelling of human visual cortex and an ability of human neurones to perceive an orientation of contours). The Gabor energy Ve may such that:

$$Ve_{\lambda,\vartheta}(f) = \sqrt{V^2_{\lambda,\vartheta,0}(f) + V^2_{\lambda,\vartheta,-\pi/2}(f)}.$$

Matrixes of co-occurrence (short for "matrixes of co-occurrence of gray levels") may be implemented in a method of Haralick, as described in the article "Textural features for image classification", by R. M. Haralick et al., IEEE Transactions on Systems, Man and Cybernetics, November 1973, vol. SMC-3, #6, p. 610-621. The matrixes may be based on the statistical analysis of the distribution of the value Ng of the pixels 12 (linked to the intensity) in the patch 11 and/or 16. Rather than using statistics based on individual pixels 12, the matrixes of co-occurrence use second-order statistics obtained by considering pairs of pixels 12. A co-occurrence matrix P(i, j/d, Θ) (which may be analogous to a bi-directional histogram) illustrates the probability (or number of occurrences) that two pixels 12, remote from each other by a distance d in a direction having an angle Θ, have intensities i and j.

The generic descriptor V obtained by a matrix of co-occurrence may comprise a plurality of texture features, such as contrast, mean and standard variation, etc. In some examples, the matrixes of co-occurrence used in a Haralick method may allow extraction of, e.g., 13 texture features for each angle Θ, such as the contrast, the mean and the standard variation already mentioned and:

the energy f1 (or second-order angular moment):

$$f1 = \sum_i \sum_j p(i, j)^2;$$

the entropy f2:

$$f2 = -\sum_i \sum_j p(i, j)\ln(p(i, j));$$

the correlation f3:

$$f3 = \frac{\sum_i \sum_j i \cdot j \cdot p(i, j) - m^2}{\sigma^2};$$

the inertia f4:

$$f4 = \sum_i \sum_j (i - m)^2 p(i, j);$$

and
the homogeneity f5:

$$f5 = \sum_i \sum_j \frac{p(i, j)}{1 + (i - j)^2};$$

where p(i, j) is an element of the matrix P,
m is the mean of p(i,j), and
σ is the standard deviation of p(i,j).

Table 1 below illustrates an example of an initial patch 11 and/or 16 with pixels 12 having values Ng e.g., comprised between 0 and 5:

TABLE 1

| 0 | 0 | 0 | 1 |
|---|---|---|---|
| 1 | 1 | 1 | 1 |
| 2 | 2 | 2 | 3 |
| 3 | 3 | 4 | 5 |

Table 2 shows a matrix of co-occurrence obtained for (d,Θ)=(1,0°).

TABLE 2

|   | 0 | 1 | 2 | 3 | 4 | 5 |
|---|---|---|---|---|---|---|
| 0 | 2 | 1 | 0 | 0 | 0 | 0 |
| 1 | 1 | 3 | 0 | 0 | 0 | 0 |
| 2 | 0 | 0 | 2 | 1 | 0 | 0 |
| 3 | 0 | 0 | 1 | 1 | 1 | 0 |
| 4 | 0 | 0 | 0 | 1 | 0 | 1 |
| 5 | 0 | 0 | 0 | 0 | 1 | 0 |

Table 3 shows a matrix of co-occurrence obtained for (d,Θ)=(1,90°).

TABLE 3

|   | 0 | 1 | 2 | 3 | 4 | 5 |
|---|---|---|---|---|---|---|
| 0 | 0 | 3 | 0 | 0 | 0 | 0 |
| 1 | 3 | 1 | 3 | 1 | 0 | 0 |
| 2 | 0 | 3 | 0 | 2 | 1 | 0 |
| 3 | 0 | 1 | 2 | 0 | 0 | 1 |
| 4 | 0 | 0 | 1 | 0 | 0 | 0 |
| 5 | 0 | 0 | 0 | 1 | 0 | 0 |

Therefore, for six angles Θ (such as: 0°, 45°, 90°, 135°, 225°, 315°), each texture descriptor V may thus be a vector having 78 dimensions (6×13=78).

In some examples, the descriptor may comprise a descriptor obtained by QMF. The QMF method may allow a textural analysis, both in the spatial domain and in the frequency domain. Alternatively or additionally, the QMF method may allow consistency of results between different types of systems 1. Alternatively or additionally, the QMF method may allow better analysis for signal having discontinuities or local oddities (e.g., blurred contours).

In examples using the QMF as an extractor, each patch 11 or 16 forms a square, with a same number of pixels on each side of the patch 11 or 16.

A wavelet transform used by the QMF decomposes a patch 11 or 16 into lower resolution sub-images. Each of the sub-images is called a wavelet coefficient and may highlight information on textures and also on contour, location and orientation in the patch 11 or 16.

In the example schematically illustrated in FIG. 9, the coefficients may be obtained by using quadrature mirror filters. A pair comprising a digital low-pass filter (H0) and a high-pass filter (H1) may be applied at each level of decomposition on an output of a previous low-pass output. In the case of a patch 11 or 16, each level of the wavelet transform by the QMF may be calculated by applying, successively on the lines and on the columns of the pixels 12 of the patch 11 or 16, the pair of low-pass H0 and high-pass H1 filters mentioned above. In other words, at each level of the wavelet transform, the recursive decomposition has, as an input, the sub-image resulting from a low-pass filter H0 in the two spatial directions (horizontal, i.e. lines, and vertical, i.e. columns).

Mathematically, the wavelet transform used in the QMF may decompose a signal using a set of elementary functions generated from a single wavelet (called the 'mother wavelet') by translation and scaling, i.e. by an affine transformation of the 'mother wavelet'. Each of the wavelets has a mean which is equal to 0, and is defined on a compact interval (contrary to a Fourier transform, which uses periodic sinusoid functions defined from [−∞; +∞]).

Let the family of wavelets $\Psi_{s,u}$ be defined by the mother wavelet $\Psi$ such that:

$$\Psi_{s,u}(x) = \frac{1}{\sqrt{s}} \Psi\left(\frac{x-u}{s}\right)$$

where s (s>0) is the parameter for the scaling; and
u is the parameter for the translation.

The wavelet transform transforms a function pa into coefficients $c_{s,u}$ such that:

$$c_{s,u} = \iint pa(x,y) \cdot \overline{\Psi_{s,u}(x,y)} \cdot dxdy.$$

The generic descriptor may comprise thus one or more texture features. The one or more texture features may comprise the mean m and the standard deviation σ of the coefficients $c_{s,u}$.

In some examples, the wavelet transform can be implemented efficiently in a pyramid-structured wavelet transform (PSWT) or in a packet wavelet transform (PWT). In the example illustrated in FIGS. 10A and 10B, at each decomposition level, the patch 11 or 16 may be decomposed into four frequency regions LL, LH, HL and HH. The PWT decomposes the signal only in the region of low frequencies LL, while the PSWT decomposes the signal in both low and high frequency regions. As mentioned above, the obtained generic descriptor comprises texture features, such as the mean m of each frequency region, and the standard deviation σ of each frequency region.

The initial patch 11 or 16 may be decomposed into any number of decomposition scales strictly superior or equal to 2. It is appreciated that the more levels, the more accurate the texture descriptor, since the obtained texture descriptor will comprise more texture features (such as the mean and the standard deviation), at the cost of a longer processing time.

In the example illustrated in FIG. 10A, the initial patch 11 or 16 may be decomposed into three decomposition scales, which is a good compromise between the processing time and the number of texture features (i.e. 20 features, such as the mean m and the standard deviation σ of LH1, HH1, HL1, LH2, HH2, HL2, LH3, HH3, HL3 and LL3). FIG. 10B illustrates an intermediate state with only two levels of decomposition of the initial patch 11 or 16.

In the examples illustrated by FIGS. 11A and 11B, each of the texture descriptor of each patch 11 or 16 may define a vector Vr or Wr, with each of the texture features of the descriptor Vr or Wr defining a dimension of the vector. For a decomposition into three levels, it is appreciated that each of the texture descriptor Vr or Wr has 20 dimensions (noted m1, σ1, m2, σ2, ... in FIGS. 11A and 11B).

In the example illustrated by FIG. 11A, the n texture descriptors Vr1, Vr2, ..., Vr16, ..., Vrn correspond to respective reference texture descriptors Vri (with i=1 ... n in the example of FIG. 11A). The reference texture descriptors Vri correspond to the class 202 of reference for cigarettes 201. The reference texture descriptors Vri of the class of reference cigarettes 201 may be extracted from one or more reference images 20 of cigarettes 201, inspected by the inspection system 1 as illustrated for example by FIG. 8.

In the example illustrated by FIG. 11B, the n texture descriptors Wr1, Wr2, ..., Wr16, ..., Wrn correspond to respective reference texture descriptors Wri (with i=1 ... n in the example of FIG. 11B). The reference texture descriptors Wri correspond to the class 202 of reference corresponding to any item 201 but cigarettes. The reference texture descriptors Wri of the class 202 of reference for any item 201 but cigarettes may be extracted from one or more reference images 20 of any item 201 not containing cigarettes, inspected by the inspection system 1.

The examples illustrated by FIGS. 11A and 11B show that the texture descriptors Vr1, Vr2, ..., Vr16, ..., Vrn and Wr1, Wr2, ..., Wr16, ..., Wrn may be stored in the database 200.

The reference classes 202 may contain any number n of reference descriptors Vri or Wri. It is appreciated that the more reference descriptors, the more accurate the classification.

The classes 202 do not need to contain the same number of descriptors between them.

Each of the patches 11 or 16 may have any number of pixels 12, such as 32×32 pixels or 128×128 pixels. It is appreciated that the more pixels 12, the more accurately the obtained descriptor, since the descriptor may comprise more pixels 12 in each of the regions for the purpose of the calculation of the mean m and the standard deviation σ, even in the regions LH3, HH3, HL3 and LL3, at the cost of a longer processing time. In the example illustrated in FIGS. 10A and 10B, the initial patch has 64×64 pixels, which is a good compromise between the processing time and the number of pixels in the LH3, HH3, HL3 and LL3 regions (i.e. 8×8 pixels in the regions LH3, HH3, HL3 and LL3 of FIG. 10A) for the calculation of mean m and the standard deviation σ in the corresponding regions.

In some embodiments, texture descriptors dedicated to a load 101 and/or a reference item 201 (such as cigarettes, as a non-limiting example) may be created.

In some examples, the dedicated descriptor may comprise one or more descriptors such as:
  a mean grey level of the patch 11 and/or 16,
  an intensity of a vertical gradient in the patch 11 (also called 'diffusion'),
  a profile P corresponding to a projection of the values Ng of the pixels 12 of the patch 11 or 16 on an axis, and/or
  a clustering of a plurality of texture descriptors.

As a non-limiting example, the above-mentioned dedicated descriptors may describe advantageously patches 11 or 16 corresponding to cigarettes, as explained below.

As shown in the example illustrated by FIG. 12A (on the left-hand side), on a vertical strip of the patches 11 or 16, the grey level is either uniform or decreases gradually. This is because, as seen the example illustrated by FIG. 3, the radiation 3 usually passes through less material at the top of the container 100, which is shown on the patches 11 or 16. The right-hand side of FIG. 12A shows that the created dedicated descriptor Pr, such as the profile P corresponding to a projection of the values Ng of the pixels 12 of the selected patch 11 on an axis (such as a horizontal axis), may be resilient to diffusion.

Furthermore, as shown in the example illustrated by FIG. 12B (on the left-hand side), the patches 11/16 may be impacted by noise. The right-hand side of FIG. 12B shows that the created descriptor P, such as the profile P corresponding to a projection of the values Ng of the pixels 12 of the patches 11 or 16 on an axis (such as a horizontal axis), may be resilient to noise.

Clustering may be advantageously used with dedicated texture descriptors, such as the profiles P described above.

Finding clusters C may aim to extract the profiles which are the most characteristics of the reference items 201 (such as cigarettes as a non-limiting example), and thus may aim to obtain patterns M for the reference items 201.

In some examples, the clustering may use K-means. As illustrated in FIGS. 12A and 12B, the profiles P are inherently periodic, and only the phase varies between them. Accordingly, a measure c of correlation of the patterns, which is invariant to translation of the patterns, may be used:

$$\text{Corr}_{(P1,P2)}(x) = \int_{-\infty}^{\infty} P1(\varepsilon) \cdot P2(\varepsilon + x) \cdot d\varepsilon$$

$$c(P1, P2) = \max_{x}(\text{corr}_{(P1,P2)}(x))$$

where P1 and P2 are the profiles of two patches, for example two patches 16. The centre of the clusters C may then be defined as the mean of the corresponding profiles P, after a translation maximizing the correlation c. An idea of the patterns M extracted by clustering is illustrated by FIG. 15B.

The advantages of clustering may include:
noise may be decreased;
generalization, over-learning may be avoided; and
the obtained patterns M may serve as a bench of filters f.
It is appreciated that filters dedicated to recognition of a specific shape show a better separability compared to generic filters (such as Gabor, MR8 . . . ).

Figure 6:
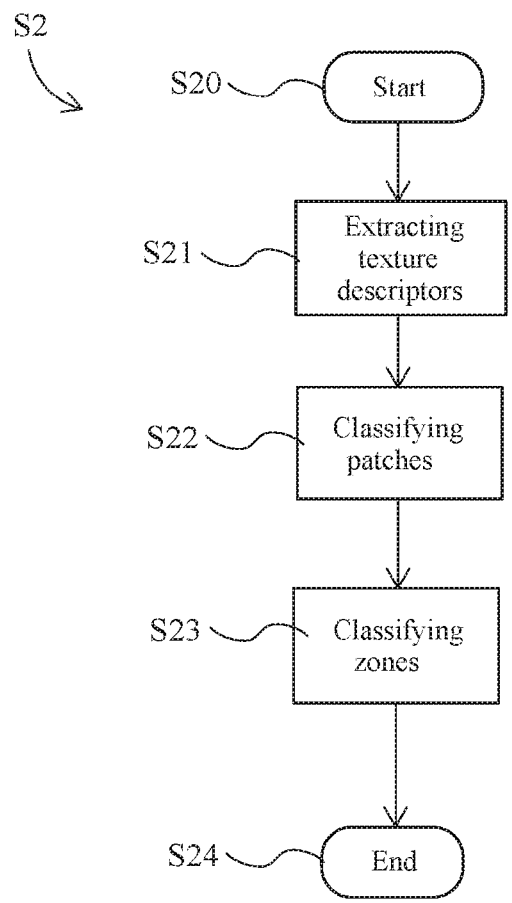
FIG. 6 is a flowchart that illustrates a detail of an example method in accordance with the present disclosure.

In the example illustrated by FIG. 6, the classifying of the patches S22 may comprise using any one of the following classifiers:
a support vector machine, SVM,
k-nearest neighbours, k-NN, and/or
a Bayesian inference.

In the example illustrated by FIGS. 13A and 13B, S22 may comprise a classifier using SVM classification as for example described in the article "Support-Vector Networks" by V. Vapnick et al., Machine Learning, 1995, 20(3), p. 273-297, and/or in the article "Learning with Kernels" by B. Scoelkopf et al., 2002, MIT Press. The SVM may aim to predict a class to which a texture descriptor, such as a vector, belongs to. The SVM may use:
first a learning step, during which a model of classes 202 may be determined from learning vectors (i.e. a set of example descriptors, i.e. the extracted reference descriptors Vri and/or Wri), and
second, a classification step.

During the learning step, the SVM may aim to find an optimal separator SP (such as a hyperplane) between the classes 202 (such as a separation SP between the class 202 for cigarettes and the class 202 for non-cigarettes) based on the learning vectors. The SVM may aim to find the optimal separator SP while the distance (also called margin) between the hyperplane SP and the nearest example is kept at a maximum. The search for the maximum margin hyperplane SP corresponds to an optimization problem in which support vectors (i.e. in the examples of FIGS. 13A and 13B, the closest learning vectors to the hyperplane SP) are selected, as explained below.

The SVM may be used, as a non-limiting example, for a binary classification such as cigarettes/non-cigarettes, as explained below.

Let D be a training set of vectors such that:

$$D = \{(Vi, yi)\}$$

where Vi is the descriptor (vector) of a patch 16 in the space $R^n$ of the texture features generated from S21; and
$yi \in \{1,-1\}$ is the reference class 202 of Vi, i.e. (1) for cigarettes and (−1) for non-cigarettes.

The SVM process may start by injection of Vi in a Hilbert space F, F having a high dimension, by a non-linear application Φ such that:

$$\Phi: R^n \rightarrow F$$

First, let us consider that the data is linearly separable in F. Thus there exists a vector ω

$$\omega \in F,$$

and a scalar b $$b \in R$$

such that:

$$yi \cdot (\langle \omega, \Phi(Vi) \rangle + b) \geq 1$$

Thus, the SVM may build the separator hyperplane SP defined by the equation:

$$\langle \omega, \Phi(Vi) \rangle + b$$

and which maximizes the error margin as illustrated by FIG. 13B.

It can be shown that the vector w defining the optimal hyperplane SP is defined by:

$$\omega = \sum_{i=1}^{N} \alpha i \cdot yi \cdot \Phi(Vi), \alpha i \geq 0$$

The vectors Vi for which $\alpha i \neq 0$ are called support-vectors.
The scalar product in F can be replaced by a kernel function K in $R^n$ such that:

$$K(Vi, Vj) = \langle \Phi(Vi), \Phi(Vj) \rangle.$$

In the example illustrated in FIGS. 13A and 13B, the separator SP illustrated in FIG. 13B is thus better than the separator SP illustrated in FIG. 13A.

However, the data may not be linearly separable in any of the spaces of characteristics generated in S21, and in some examples a Gaussian or a polynomial kernel may be used.

The SVM may use functions as set out in a libsvm library by C. C. Chang and C. J. Lin, available online at:
http://www.csie.ntu.edu.tw/~cjlin/libsvm/.

In some examples, the Gaussian kernel may be such that:

$$K(Vi, Vj) = \exp\left(-\frac{(Vi - Vj)^2}{2\tau^2}\right)$$

where τ may be obtained by k-fold cross-validation.
In some other examples, the polynomial kernel function may be:

$$(\gamma \cdot u \cdot v + Co)^n$$

where (γ,v)) are chosen parameters;
Co is a chosen coefficient, usually 0; and
n is the degree of the polynomial kernel function, usually 3.

The determination of the parameters (γ,v) may be performed by cross-validation. The cross-validation may comprise dividing the available data into multiple subsets (e.g., 5), and evaluating the SVM on each subset using the remaining data as a learning set. The evaluation may be performed several times by varying (γ,v), then keeping the best couple (γ,v).

Once the classifier (such as the separator SP) is determined, to classify a texture descriptor (vector) of a patch 11, the learning vectors used in the search of the hyperplane SP are no longer useful, only the found support vectors are used. The SVM method may be thus effective in terms of complexity and processing time.

In some examples, a classifier may use a k-NN, which may aim to assign a texture of a patch 11 represented by a vector V to the most representative class 202 Vri in its immediate vicinity, as illustrated in FIG. 14. The k-NN method can be formally defined by:

$$V \in Vri$$

$$\text{if } \forall j \neq i, Si(x) > Sj(x)$$

where $Si(x)$ is the number of neighbours of V belonging to the class Vri, among its k nearest neighbours.

The k-NN method may thus select the k closest learning vectors Vri or Wri to the vector V to be classified. The technique of classification by k-NN may thus be a method of classification based on distances. The k-NN classifier may use any type of distance, such as the L1 distance (Manhattan), $$L1 = \sum_{i=1}^{n} |xi - yi|$$

the L2 distance (Euclidian)

$$L2 = \sqrt{\sum_{i=1}^{n} (xi - yi)^2}$$

and/or the L3 distance (Minkowski)

$$L3 = \sqrt[p]{\sum_{i=1}^{n} |xi - yi|^p}, \text{ with } p = 3.$$

It is appreciated that other values of p may be used.

The patch 11 will then be classified in the class 202 of the majority of the k-nearest neighbours. The choice of k may depend on the images, since a large value of k may reduce noise but may also make the decision borders less distinctive. k is an odd integer. An optimal k may be estimated by cross-validation, and k may be preferably equal to 5.

In the example illustrated by FIGS. 11A, 11B and 11C, it may thus be determined whether the vector V of the patch 11 of FIG. 11C, to be classified, has, among its 5 closest neighbours (using for example L3):

more neighbours in class 1 (cigarettes), in which case the patch 11 is classified as cigarettes, or more neighbours in class 2 (non-cigarettes), in which case the patch 11 is classified as non-cigarettes.

In some examples, a classifier may use a Bayesian inference. In the example illustrated in FIGS. 15A, 15B and 15C, for each patch 11 to be classified, the correlation with each pattern M of the bench of filters is determined, and the best response Br is selected. If the selected best response Br goes over a threshold T, then it will be classified in a corresponding class 202, for example as cigarettes, i.e. class 1. If the selected best response Br does not go over the threshold T, it will be classified as non-cigarettes, i.e. class 2.

The classifier using Bayesian inference may be based on the principle of the classifiers using margins, as illustrated in FIG. 15C. In other words, the distance of the selected best response Br to the threshold T determines a value of confidence Vc of the classification, i.e. the further the selected best response is from the threshold T, the less the classifier is certain of its decision.

In some examples, the thresholds T may be determined by Bayesian inference for each pattern M as explained below.

Let Mi be the ith pattern, and $pa_i^k$ the k-th patch of all the patches 16 of the learning set, for which Mi has obtained the best responses $Br_i^k$.

The decision threshold Ti is the one which minimizes the rate of wrong classification.

$$Ti = \underset{\alpha}{\arg\min} \, p(C2 / pa_i^k \in G1) + p(C1 / pa_i^k \in G2)$$

or $$Ti = \underset{\alpha}{\arg\min} \, p(Br_k^k < \alpha / pa_i^k \in G1) + p(Br_i^k > \alpha / pa_i^k \in G2)$$

where G1 and G2 correspond to all the patches 16 cigarettes and non-cigarettes, respectively.

FIG. 15A illustrates a patch 11 to be classified and its profile P. As already stated, FIG. 15B illustrates an example of an obtained bench of filters f, the patterns Mi as extracted by clustering, and the decision thresholds Ti. FIG. 15C illustrates the classification of the patch 11 and the determination of the value of confidence VC.

The classification of the patches 11 as performed in S21 and S22 is performed locally, i.e. that any selected patch 11 is classified using only its own texture descriptor. In other words, at the end of the classification S22, there may be isolated patches 11 falsely detected as cigarettes (sometimes referred to as "false positives" 18, as illustrated in the example of FIGS. 16A and 16B), but also patches "cigarettes" not recognized as such in large zones of cigarettes.

In the example illustrated in FIG. 6, the classifying may thus further comprise classifying, at S23, one or more zones 13 of patches 11, each zone 13 comprising a plurality of selected patches 11 using an uniformization algorithm. The uniformization may take into account zones 13 of patches 11 to determine their class.

In some examples, the uniformization algorithm may be at least one of the following:

a binary morphological closing, a segmentation, and/or a regularization.

In a binary morphological closing, elements which are both connected to classified patches, e.g., cigarettes patches, and below a certain size may be classified in the same connected class.

In a segmentation process, the image is first segmented into zones 13, and each zone 13 is classified based on a ratio ra, such that ra=(number of patches "cigarette"/number of patches "non-cigarettes") in the zone 13.

A regularization type of process may be based on the assumption that a patch 11 surrounded by patches "cigarettes" is very likely to be also a patch "cigarettes".

In some examples, the regularization may be based on at least one of the following:

the Markov fields, and/or the Gibbs fields.

In some examples, the image 10 of FIGS. 16A and 16B containing the classified patches 11 may be modified into an intermediate modified image, so that the intermediate modified image may show a value of confidence (such as a distance to the nearest neighbour in the case of k-NN, or a distance to the hyperplane SP in the case of the SVM), indicating how sure the classifier is about its classification. In some examples, the values of confidence may be probabilities that a patch 11 is, for example, cigarettes or non-cigarettes.

Once the initial image 10 has been modified in a probabilistic space in the intermediate modified image, Markov fields may be applied to measure a probability of an overall final result image 104, as illustrated in FIG. 17A, e.g., by using a local probability of each patch 11, using only the information of each patch's neighbourhood.

Let
X be a Markov field,
I the final result image 104 illustrated in FIG. 17A,
$D_I$ the domain of I,
pa a patch 11 of the intermediate modified image, and
N(pa) the neighbourhood of the patch pa.
The probability of I will thus be:

$$p(X = I) = \prod_{pa \in D_I} p(X_{pa} = I_{pa} / I) = \prod_{pa \in D_I} p(X_{pa} = I_{pa} / \{I_n\}),$$

$n \in N(pa)$.

This shows that it is unlikely that a "cigarettes" patch is in the middle of "non-cigarettes" patches and vice-versa.

As illustrated in the example of FIG. 17A, the final result image 104 may be the most probable image 104.

Alternatively or additionally, the images 10 and/or 104 may be processed using Gibbs fields.

Alternatively or additionally, once the initial image 10 has been modified in a probabilistic space in the intermediate modified image, Gibbs fields may be applied to measure a probability of an overall final result image 104, as illustrated in FIG. 17A. In some examples, Gibbs fields may have a smaller computational cost compared to Markov fields. A regularization type of process may minimize an Energy function. An Energy function U of Gibbs may be such that:

$$P(X = x) = \frac{1}{Z} \exp(-U(x))$$

$$U(x) = \sum U_{local}(x)$$

Maximizing the likelihood of an image may amount to minimizing the global energy U. There may be several methods to minimize the global energy.

In some examples minimizing the global energy may be performed using an Ising model.

Let

B:E→{1,−1} the binary image B generated from the classification, as illustrated in FIG. 17B, and

I:E→[0 . . . 1]

the image I (referred to as image 104 in FIG. 17A) of probability indicating the confidence in the classification of the patch 11 (referred to as "pa"). Considering the 4-connexity as a neighbourhood, there are only first-order potentials (i.e. the patch 11 "pa" itself) and second-order potentials (i.e. the patch 11 "pa" and its neighbour N(pa)). The potentials U are defined as follows:

$U_{pa}(x_{pa})=0$ if $x_{pa}=B_{pa}$ $U_{pa}(x_{pa})=-\log(1-P(pa))$ otherwise $U_{(pa,N(pa))}(x_{pa},x_{pa})=+1$ if $x_{pa} \neq x_{N(pa)}$ $U_{(pa,N(pa))}(x_{pa},x_{pa})=-1$ if $x_{pa}=x_{N(pa)}$ and the global energy to minimize is $$U(X) = \alpha \sum_{pa} U_{pa}(x_{pa}) + \beta \sum_{(pa,N(pa))} U_{(pa, N(pa))}(x_{pa}, x_{N(pa)}) + \delta \sum_{pa} x_{pa}$$

where α is an data-attachment parameter;
β is a coupling parameter between neighbouring patches; and
δ is an external magnetic field.

When β is positive, the most probable configurations (i.e. with the lowest energies) are those for which neighbouring patches are of the same class 202. The absolute value of β determines the strength of regularization of the model.

α shows that the result image 105 should not be fundamentally different from the image 104 before regularization. Thus, α may be used to invert the classes of the patches 11 only where the classifier is the least certain of its classification.

δ enables promoting, a priori, a class or another, whether it is preferable to extend the zones 13 "cigarettes" or the "non-cigarettes" zones 13.

In some examples minimizing the global energy may be performed using an Energy function.

In some examples, a simulated "annealing" may be used, for example for a Gibbs field.

In some examples, a Gibbs distribution may be introduced with a temperature TO, such that:

$$P_{TO}(X = x) = \frac{1}{Z} \exp\left(-\frac{U(x)}{TO}\right)$$

The algorithm may build a sequence of images thanks to a sampler (such as the "sampler of Metropolis") which may converge towards the distribution $P_{TO}$. A subsequent lowering of the temperature TO in the algorithm may ensure that the last image generated by the sampler may be a global minimum of the image.

Alternatively or additionally, other algorithms, such as iterated conditioned modes, may also be used during the regularization.

The action may be triggered using the result image 105. Regularization may enable to cancel false positives and/or false negatives 18 in the final image as illustrated in FIG. 18.

Regularization may also enable identification and/or detection of items and/or compositions, even when at least a part of the load is superimposed with a screen blocking the transmission of the inspection radiation.

Variations and Modifications

Other variations and modifications of the system or the analyser will be apparent to the skilled in the art in the context of the present disclosure, and various features described above may have advantages with or without other features described above.

For example, the analyser 5 may, at least partly, form a part of the inspection system 1.

It is understood that the inspection radiation source may comprise sources of other radiation, such as gamma rays or neutrons. The inspection radiation source may also comprise sources which are not adapted to be activated by a power supply, such as radioactive sources, such as using Co60 or Cs137.

As one possibility, there is provided a computer program, computer program product, or computer readable medium, comprising computer program instructions to cause a programmable computer to carry out any one or more of the methods described herein. In example implementations, at least some portions of the activities related to the analyser 5 and/or the communications networks 6 and/or 7 herein may be implemented in software. It is appreciated that software components of the present disclosure may, if desired, be implemented in ROM (read only memory) form. The software components may, generally, be implemented in hardware, if desired, using conventional techniques.

In some examples, components of the analyser 5 and/or the communications networks 6 and/or 7 may use specialized applications and hardware.

As will be apparent to the skilled in the art, the server 8 should not be understood as a single entity, but rather refers to a physical and/or virtual device comprising at least a processor and a memory, the memory may be comprised in one or more servers which can be located in a single location or can be remote from each other to form a distributed network (such as "server farms", e.g., using wired or wireless technology).

In some examples, one or more memory elements (e.g., the database 200 and/or the memory of the processor) can store data used for the operations described herein. This includes the memory element being able to store software, logic, code, or processor instructions that are executed to carry out the activities described in the disclosure.

A processor can execute any type of instructions associated with the data to achieve the operations detailed herein in the disclosure. In one example, the processor could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

The communications network 6 and the communications network 7 may form only one network.

The data received by the analyser 5 may be typically received over a range of possible communications networks 6 and/or 7 at least such as: a satellite based communications network; a cable based communications network; a telephony based communications network; a mobile-telephony based communications network; an Internet Protocol (IP) communications network; and/or a computer based communications network.

In some examples, the communications networks 6 and/or 7 and/or the analyser 5 may comprise one or more networks. Networks may be provisioned in any form including, but not limited to, local area networks (LANs), wireless local area networks (WLANs), virtual local area networks (VLANs), metropolitan area networks (MANs), wide area networks (WANs), virtual private networks (VPNs), Intranet, Extranet, any other appropriate architecture or system, or any combination thereof that facilitates communications in a network.

The above embodiments are to be understood as illustrative examples, and further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A method for inspecting a load in a container, comprising:
    classifying one or more overlapping successive patches of a digitized inspection image, the digitized inspection image being generated by an inspection system configured to inspect the container by transmission of inspection radiation from an inspection radiation source to an inspection radiation detector through the container,
    wherein the classifying comprises:
        extracting one or more texture descriptors of a patch, and
        classifying the patch, by comparing the one or more extracted texture descriptors of the patch to one or more reference texture descriptors corresponding to one or more classes of reference items, the one or more reference texture descriptors of each class of reference items being extracted from one or more reference images of the one or more reference items.

2. The method of claim 1, further comprising triggering an action based on the classifying, wherein the action is chosen from the group consisting of:
    determining a composition of a part of the load corresponding to the patch of the inspection image,
    displaying the digitized inspection image with one or more determined compositions for one or more parts of the load,
    issuing an alarm,
    sending one or more classified patches to a controller, and any combination of the foregoing.

3. The method of claim 1, wherein the one or more texture descriptors are chosen from the group consisting of: a generic descriptor, a descriptor dedicated to a load, a descriptor dedicated to a reference item, any combination of the foregoing.

4. The method of claim 3, wherein the generic descriptor is extracted using one or more extractors chosen from the group consisting of:
    a response to a bench of filters,
    a Haralick method implementing a matrix of co-occurrence,
    a quadrature mirror filter, and
    any combination of the foregoing.

5. The method of claim 3, wherein the inspection image comprises a plurality of pixels, at least a value representative of the transmission of the inspection radiation through the container being associated with each pixel, and wherein the dedicated descriptor comprises one or more descriptors chosen from the group consisting of:
    a mean grey level of the selected patch,
    an intensity of a vertical gradient in the selected patch, a profile corresponding to a projection of values of pixels of the patch on an axis,
a clustering of a plurality of texture descriptors, and
any combination of the foregoing.

6. The method of claim 1, wherein each patch forms a square, with a same number of pixels on each side of the patch, wherein the number of pixels on each side of the patch is comprised between 32 and 128, and is preferably equal to 64.

7. The method of claim 1, wherein the overlap between two successive patches is comprised between 10% and 90%, preferably equal to 50%.

8. The method of claim 1, wherein the classifying further comprises classifying one or more zones of patches using an uniformization algorithm, each zone comprising a plurality of selected patches, wherein the uniformization algorithm is chosen from the group consisting of:
a binary morphological closing,
a segmentation,
a regularization based on at least one of Markov fields or Gibbs fields, and
any combination of the foregoing.

9. The method of claim 1, wherein a type of inspection system is characterized by an energy and a dose of the inspection radiation.

10. The method of claim 9, wherein the inspection radiation comprises X-rays.

11. The method of claim 9, wherein the energy is comprised between 1 MeV and 15 MeV, and wherein the dose is comprised between 2 mGy and 20 Gy.

12. The method of claim 11, wherein for a first type of inspection system the energy is 9 MeV and the dose is 17 Gy, and wherein for another type of inspection system the energy is 4 MeV and the dose is 20 mGy.

13. The method of claim 9 wherein one or more reference texture descriptors for each type of inspection system are stored in a reference database.

14. The method of claim 1, wherein a reference item is chosen from the group consisting of cigarettes, bank notes, drugs, medications, pills, beans, and any combination of the foregoing.

15. A method for inspecting a load in a container, comprising:
classifying one or more patches of a digitized inspection image, the digitized inspection image being generated by an inspection system configured to inspect the container by transmission of inspection radiation from an inspection radiation source to an inspection radiation detector through the container,
wherein the classifying comprises:
extracting one or more texture descriptors of a patch,
classifying the patch, by comparing the one or more extracted texture descriptors of the patch to one or more reference texture descriptors corresponding to one or more classes of reference items, the one or more reference texture descriptors of each class of reference items being extracted from one or more reference images of the one or more reference items and
using one or more classifiers chosen from the group consisting of:
a support vector machine,
k-nearest neighbours, using at least one of an L1 distance, an L2 distance, or an L3 distance,
a Bayesian inference, and
any combination of the foregoing.

16. The method of claim 15, wherein k is an odd integer.

17. The method of claim 15, further comprising triggering an action based on the classifying, wherein the action is chosen from the group consisting of:
determining a composition of a part of the load corresponding to the patch of the inspection image,
displaying the digitized inspection image with one or more determined compositions for one or more parts of the load,
issuing an alarm,
sending one or more classified patches to a controller, and
any combination of the foregoing.

18. The method of claim 15, wherein the one or more texture descriptors are chosen from the group consisting of: a generic descriptor, a descriptor dedicated to a load, a descriptor dedicated to a reference item, any combination of the foregoing.

19. The method of claim 15, wherein each patch forms a square, with a same number of pixels on each side of the patch, wherein the number of pixels on each side of the patch is comprised between 32 and 128, and is preferably equal to 64.

20. The method of claim 15, wherein the classifying further comprises classifying one or more zones of patches using an uniformization algorithm, each zone comprising a plurality of selected patches, wherein the uniformization algorithm is chosen from the group consisting of:
a binary morphological closing,
a segmentation,
a regularization based on at least one of Markov fields or Gibbs fields, and
any combination of the foregoing.

21. The method of claim 15, wherein a type of inspection system is characterized by an energy and a dose of the inspection radiation.

22. The method of claim 15, wherein a reference item is chosen from the group consisting of cigarettes, bank notes, drugs, medications, pills, beans, and any combination of the foregoing.

23. A method for inspecting a load in a container, comprising:
classifying one or more patches of a digitized inspection image, the digitized inspection image being generated by an inspection system configured to inspect the container by transmission of inspection radiation from an inspection radiation source to an inspection radiation detector through the container,
wherein the classifying comprises:
extracting one or more texture descriptors of a patch, and
classifying the patch, by comparing the one or more extracted texture descriptors of the patch to one or more reference texture descriptors corresponding to one or more classes of reference items, the one or more reference texture descriptors of each class of reference items being extracted from one or more reference images of the one or more reference items,
wherein the inspection image comprises a plurality of pixels, at least a value representative of the transmission of the inspection radiation through the container being associated with each pixel, the method further comprising selecting only patches having a mean values Mg such that:

$T1 < Mg < T2$, wherein Mg is a mean of the at least a value associated with the pixels of the patch, T1 is a minimum threshold value for at least one item of interest inspected by the inspection system, and T2 is a maximum threshold value for the at least one item of interest inspected by the inspection system.

24. The method of claim 23, further comprising triggering an action based on the classifying, wherein the action is chosen from the group consisting of:
   determining a composition of a part of the load corresponding to the patch of the inspection image,
   displaying the digitized inspection image with one or more determined compositions for one or more parts of the load,
   issuing an alarm,
   sending one or more classified patches to a controller, and
   any combination of the foregoing.

25. The method of claim 23, wherein the one or more texture descriptors are chosen from the group consisting of: a generic descriptor, a descriptor dedicated to a load, a descriptor dedicated to a reference item, any combination of the foregoing.

26. The method of claim 23, wherein each patch forms a square, with a same number of pixels on each side of the patch, wherein the number of pixels on each side of the patch is comprised between 32 and 128, and is preferably equal to 64.

27. The method of claim 23, wherein the classifying further comprises classifying one or more zones of patches using an uniformization algorithm, each zone comprising a plurality of selected patches, wherein the uniformization algorithm is chosen from the group consisting of:
   a binary morphological closing,
   a segmentation,
   a regularization based on at least one of Markov fields or Gibbs fields, and
   any combination of the foregoing.

28. The method of claim 23, wherein a type of inspection system is characterized by an energy and a dose of the inspection radiation.

29. The method of claim 23, wherein a reference item is chosen from the group consisting of cigarettes, bank notes, drugs, medications, pills, beans, and any combination of the foregoing.

* * * * *